US010486142B2

(12) United States Patent
Goyal

(10) Patent No.: US 10,486,142 B2
(45) Date of Patent: Nov. 26, 2019

(54) COMPOSITIONS AND METHODS RELATED TO THE PRODUCTION OF ACRYLONITRILE

(71) Applicant: SOUTHERN RESEARCH INSTITUTE, Birmingham, AL (US)

(72) Inventor: Amit Goyal, Cary, NC (US)

(73) Assignee: Southern Research Institute, Birmingham, AL (US)

(*) Notice: Subject to any disclaimer, the term of this patent is extended or adjusted under 35 U.S.C. 154(b) by 0 days.

(21) Appl. No.: 15/950,788

(22) Filed: Apr. 11, 2018

(65) Prior Publication Data
US 2018/0229222 A1    Aug. 16, 2018

Related U.S. Application Data

(62) Division of application No. 15/096,839, filed on Apr. 12, 2016, now abandoned.

(60) Provisional application No. 62/182,092, filed on Jun. 19, 2015.

(51) Int. Cl.
C07C 45/52       (2006.01)
C07C 253/26      (2006.01)
B01J 23/888      (2006.01)
B01J 23/00       (2006.01)
B01J 23/89       (2006.01)
C07C 47/22       (2006.01)
C07C 255/08      (2006.01)
B01J 37/08       (2006.01)
B01J 37/02       (2006.01)
B01J 35/10       (2006.01)

(52) U.S. Cl.
CPC ........... B01J 23/888 (2013.01); B01J 23/002 (2013.01); B01J 23/892 (2013.01); B01J 23/8926 (2013.01); C07C 45/52 (2013.01); C07C 47/22 (2013.01); C07C 253/26 (2013.01); C07C 255/08 (2013.01); B01J 35/1019 (2013.01); B01J 35/1061 (2013.01); B01J 37/0203 (2013.01); B01J 37/0205 (2013.01); B01J 37/088 (2013.01); B01J 2523/00 (2013.01); Y02P 20/52 (2015.11)

(58) Field of Classification Search
CPC ............... C07C 253/26; C07C 45/52
See application file for complete search history.

(56) References Cited

U.S. PATENT DOCUMENTS

| 1,916,743 A | 7/1933 | Schwenk et al. |
| 4,430,253 A | 2/1984 | Dubeck et al. |
| 5,977,013 A | 11/1999 | Elliott et al. |
| 7,790,934 B2 | 9/2010 | Redlingshofer et al. |
| 7,846,861 B2 | 12/2010 | Redlingshofer et al. |
| 8,378,136 B2 | 2/2013 | Dubois |
| 8,461,380 B2 | 6/2013 | Aoki et al. |
| 8,530,697 B2 | 9/2013 | Dubois et al. |
| 9,708,249 B1 | 7/2017 | Goyal et al. |
| 2003/0119952 A1 | 6/2003 | Werpy et al. |
| 2008/0183019 A1 | 7/2008 | Redlingshofer et al. |
| 2009/0005614 A1 | 1/2009 | Hulteberg et al. |
| 2010/0113833 A1 | 5/2010 | Redlingshofer et al. |
| 2011/0136954 A1 | 6/2011 | Dubois |
| 2011/0160491 A1 | 6/2011 | Dubois et al. |
| 2011/0190546 A1 | 8/2011 | Dakka |
| 2014/0206831 A1 | 7/2014 | Venkitasubramanian |

FOREIGN PATENT DOCUMENTS

| CN | 101652172 A | 2/2010 |
| CN | 103619799 A | 3/2014 |
| CN | 103827070 A | 5/2014 |
| CN | 104710277 A | 6/2015 |
| GB | 897226 A | 5/1962 |
| WO | WO-2000/017106 A1 | 3/2000 |

OTHER PUBLICATIONS

Abraham, D. S., "Production of propylene oxide from propylene glycol" Master's Thesis University of Missouri-Columbia (2007) (75 pages).
Acrylonitrile by propene ammoxidation, http://tekim.undip.ac.id/staf/istadi/files/2009/05/topik51.pdf (2009) (26 pages).
Adams, C.R. and Jennings, T.J., Investigation of the Mechanism of Catalytic Oxidation of Proylene to Acrolein and Acryonitrile. J Catal. 1963; 2:63-8.
Benchaita, T., Greenhouse gas emissions from new petrochemical plants. Technical Note No. IDB-TN- 562 (2013) (84 pages).
Copeland, J. R. et al., Surface Interactions of $C_2$ and $C_3$ Polyols with $\gamma$-$Al_2O_3$ and the Role of Coadsorbed Water. Langmuir. 2013; 29:581-93.
Cutrufello, M. G. et al., Acid-Base Properties of Zirconium, Cerium and Lanthanum Oxides by Calorimetric and Catalytic Investigation. Top Catal. 2002; 19(3-4):225-40.
Dar, A.B. et al., Vapour Phase Conversion of Glycerol to Acrolein over Supported Copper. Arab J Sci Eng. 2013; 38:37-40.
Dasari, M.A. et al., Low-Pressure Hydrogenolysis of Glycerol to Propylene Glycol. Appl Catal A: General. 2005; 281 225-23.
Eriksson, Ö. and Goring, D.A.I., Structural studies on the chemical bonds between lignins and carbohydrates in spruce wood. Wood Sci Technol. 1980; 14:267-79.
Gallezot, P. et al., Glucose hydrogenation on promoted raney-nickel catalysts. J Catal. 1994; 146:93-102.
Garrote, G. et al., Mild autohydrolysis: an environmentally friendly technology for xylooligosaccharide production from wood. J Chem Biotechnol. 1999; 74:1101-9.

(Continued)

Primary Examiner — Joseph R Kosack
(74) Attorney, Agent, or Firm — Ballard Spahr LLP

(57) ABSTRACT

Disclosed herein is a method useful in the process of contacting a first product that includes ethylene glycol, propylene glycol, and glycerol with the catalyst composition, thereby producing a second product that includes acrolein and acetaldehyde.

20 Claims, 9 Drawing Sheets

(56) References Cited

OTHER PUBLICATIONS

Grasselli et al., Acrylonitrile from Biomass: Still Far from Being a Sustainable Process. Top Catal. 2016; 59(17):1651-8.

Husman, G., Development and Commercialization of a Novel Low-Cost Carbon Fiber. Project ID # LM048. Zoltek Companies, Inc., May 16, 2012 (21 pages).

Iqbal, Z. et al., Chapter 10: Carbon Nanotubes/Nanofibers and Carbon Fibers. Functional Fillers for Plastics. Dept. of Chem. and Environ. Sci., New Jersey Inst. of Technol. (2010) (35 pages).

JCATI Funded Research (2016) available at: http://www.jcati.org/funding/jcati-funded-research (8 pages).

Jubb, C. et al., Chapter 3: Chemical Industry Emissions. IPCC Guidelines for National Greenhouse Gas Inventories; vol. 3: Industrial Processes and Product Use. (2006) (110 pages).

Li, Z. et al., Dehydration and dehydrogenation of ethylene glycol on rutile $TiO_2(110)$. Phys Chem Chem Phys. 2013; 15:12180-6.

Liebig, C. et al., Glycerol conversion to acrylonitrile by consecutive dehydration over $WO_3/TiO_2$ and ammoxidation over Sb-(Fe,V)-O. Appl Catal B: Environmental. 2013; 132-133:170-82.

Niemelä, K. et al., Chapter 7: Characterization of Pulping Liquors. Analytical Methods in Wood Chemistry, Pulping and Papermaking. Eero Sjöström and Raimo Alén, Eds. Springer-Verlag, Berlin (1999) pp. 193-231.

Oka, H. et al., Ammoxidation of Acrolein on Catalyst of Fe—Bi—P Mixed Oxide System. J Appl Chem Biotechnol. 1975; 25:663-70.

Olga, M. et al., New Reaction: Conversion of Glycerol into Acrylonitrile. Chem Sus Chem. 2008; 1:511-3.

Palmqvist, E. et al., Fermentation of lignocellulosic hydrolysates. II: inhibitors and mechanisms of inhibition. Bioresource Technol. 2000; 74:25-33.

Ravenelle, R.M. et al., Effects of Metal Precursors on the Stability and Observed Reactivity of $Pt/\gamma-Al_2O_3$ Catalysts in Aqueous Phase Reactions. ChemCatChem. 2012; 4:492-4.

Ravenelle, R.M. et al., Structural Changes of $\gamma-Al_2O_3$-Supported Catalysts in Hot Liquid Water. Catalysis. 2011; 1:552-61.

Sugar to Polyols Process—IPCI, (2012) available at http://polyolchem.com/technology/sugar-to-polyols-process (3 pages).

Sun et al., Production of propanal from 1,2-propanediol over silica-supported $WO_3$ catalyst. Appl Catal A: General. 2014; 487:234-41.

Suprun et al., TPD-TG-MS Investigations of the Catalytic Conversion of Glycerol over $MO_x$, —$Al_2O_3$—$PO_4$ Catalysts. Chem Eng Technol. 2011; 34(1):134-9.

Tao et al., Comparison of Gas-Phase Dehydration of Propane Polyols Over Solid Acid-Base Catalysts. Catal Today. 2014; 234: 237-44.

Torresi, P.A. et al., Conversion of diols by dehydrogenation and dehydration reactions on silica-supported copper catalysts. Appl Catal A: General. 2013; 458:119-29.

Ulgen, Conversion of glycerol to the valuable intermediates acrolein and allyl alcohol in the presence of heterogeneous catalysts. Dissertation 2009; (144 pages).

Ulgen, A. et al., Conversion of glycerol to acrolein in the presence of $WO_3/TiO_2$ catalysts. Appl Catal A: General. 2011; 400:34-8.

Ulgen, A. et al., Conversion of Glycerol to Acrolein in the Presence of $WO_3/ZrO_2$ Catalysts. Catal Lett. 2009; 131:122-8.

Wang et al., Catalytic performance of vanadium pyrophosphate oxides (VPO) in the oxidative dehydration of glycerol. Appl Catal A: General. 2010; 376:25-32.

Xia, S. et al., Hydrogenolysis of glycerol over $Cu_{0.4}/Zn_{5.6-x}Mg_xAl_2O_{8.6}$ catalysts: The role of basicity and hydrogen spillover. J Catal. 2012; 296:1-11.

Zhang, Z. et al, Aqueous-phase hydrogenation of lactic acid to propylene glycol. Appl Catal A: General. 2001; 219:89-98.

International Search Report and Written Opinion dated Oct. 24, 2017 by the International Searching Authority for International Patent Application No. PCT/US2017/046905, which was filed on Aug. 15, 2017 and published as WO 2018/038968 dated Mar. 1, 2018 (Inventor—Goyal et al.;Applicant—Southern Research Institute;) (8 pages).

COMPOSITIONS AND METHODS RELATED TO THE PRODUCTION OF ACRYLONITRILE

CROSS-REFERENCE TO RELATED APPLICATIONS

This is a divisional application of U.S. application Ser. No. 15/096,839, filed Apr. 12, 2016, which claims the benefit of U.S. Provisional Application No. 62/182,092, filed Jun. 19, 2015, which are both incorporated herein by reference in their entirety.

FEDERALLY SPONSORED RESEARCH

This invention was made with government support under DE-EE0006781 awarded by Department of Energy and the office of Energy Efficiency and Renewable Energy (DOE-EERE). The government has certain rights in the invention.

FIELD OF THE INVENTIONS

The compositions, articles, and methods disclosed herein relates to the production of acrylonitrile and other useful chemicals.

BACKGROUND

The US Department of Energy and the industrial sector anticipate an 11-18% annual increase in the market for carbon fiber, specifically driven by motivation to reduce weight for vehicles (Global market opportunities for carbon fiber: Carbon fiber world conference, Washington D.C. 2011). Currently, carbon fibers that meet specifications (250 ksi tensile strength and 25 Msi Young's modulus) for automotive applications are made from polyacrylonitrile (PAN), obtained from acrylonitrile (ACN), which is synthesized using propylene and ammonia. World ACN production in 2010 was 5.7 million tons, and is highly dependent on volatility of propylene prices. Additionally, propylene production (a byproduct of naphtha cracking for ethylene) is reducing due to growth of the natural gas based process for production of ethylene. In light of these facts and increased demand for carbon fibers, US DOE has expressed interest in making ACN precursor that can meet specifications needed for production of carbon fibers from renewable non-food biomass with a goal of $1.00/lb cost.

There is a need for improved catalysts and methods for producing ACN and intermediates to make ACN. Such a catalytic composition and method are described herein.

SUMMARY OF THE INVENTION

Disclosed herein is a catalyst composition for converting propylene glycol and glycerol to acrolein comprising a catalyst having the formula:

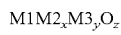

wherein M1 is a metal promoting dehydrogenation and C—O cleavage, wherein M2 is a metal with acid sites promoting dehydration, wherein M3 is an amphoteric catalyst support, with acid and base sites, promoting both dehydration and dehydrogenation in conjunction with M1, wherein x is a molar ratio from about 0.25 to about 4, wherein y is a molar ratio from about 0.25 to about 4, wherein z is the total amount of oxygen bound to M1, M2, and M3, and corresponds to the sum of the oxidation states of M1, M2, and M3.

Disclosed herein is a method comprising the step of: a) in a single step, converting C5 and/or C6 sugars to a first product comprising ethylene glycol, propylene glycol, and glycerol in the presence of a multifunctional catalyst.

Disclosed herein is a method comprising the step of: a) contacting a first product comprising ethylene glycol, propylene glycol, and glycerol with the catalyst disclosed herein, thereby producing a second product comprising acrolein and acetaldehyde.

Disclosed herein is a method comprising the step of: a) contacting propylene glycol with a catalyst composition, thereby producing acrolein.

Additional advantages will be set forth in part in the description which follows, and in part will be obvious from the description, or can be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DESCRIPTION OF THE FIGURES

The accompanying figures, which are incorporated in and constitute a part of this specification, illustrate several aspects and together with the description serve to explain the principles of the invention.

Figure 1:
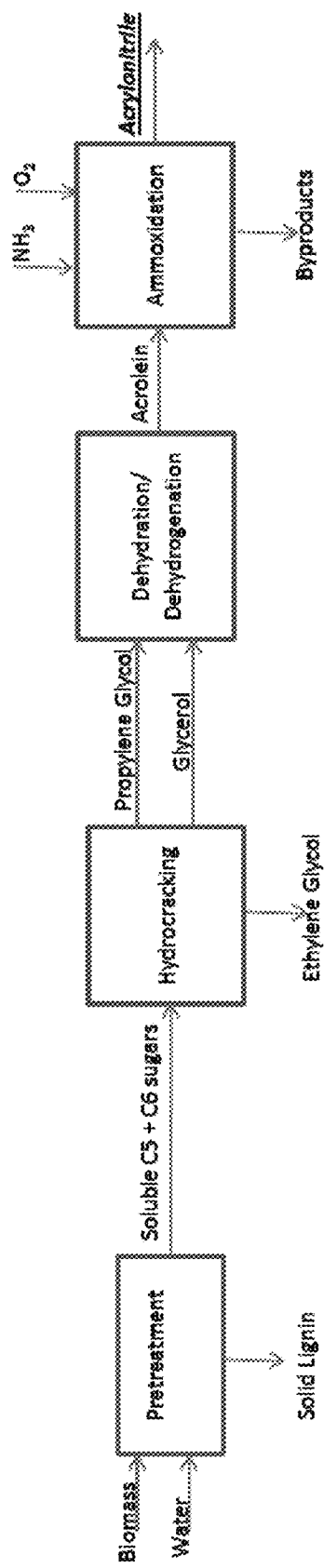
FIG. 1 shows the overall flow schematic of non-limiting aspects of the method disclosed herein for the process of producing acrylonitrile.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The disclosed methods and articles can be understood more readily by reference to the following detailed description.

Before the present compounds, compositions, articles, systems, devices, and/or methods are disclosed and described, it is to be understood that they are not limited to specific articles or methods unless otherwise specified. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

1. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to "a therapeutic agent" includes mixtures of therapeutic agents, reference to "a pharmaceutical carrier" includes mixtures of two or more such carriers, and the like].

"Optional" or "optionally" means that the subsequently described event or circumstance can or cannot occur, and that the description includes instances where the event or circumstance occurs and instances where it does not. For example, the phrase "optionally comprising an adhesive material" means that the adhesive material can or cannot be present and that the description includes both situations.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A weight percent (wt. %) of a component, unless specifically stated to the contrary, is based on the total weight of the therapeutic composition or composition or material, in which the component is included.

References in the specification and concluding claims to parts by weight, of a particular element or component in a composition or article, denote the weight relationship between the element or component and any other elements or components in the composition or article for which a part by weight is expressed. Thus, in a composition containing 2 parts by weight of component X and 5 parts by weight component Y, X and Y are present at a weight ratio of 2:5, and are present in such ratio regardless of whether additional components are contained in the composition.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

2. Production of Intermediates to Produce Acrylonitrile

Micron-sized carbon fibers presently used are mostly produced by heat treatment or controlled pyrolysis of different precursor fibers. The most prevalent precursors are PAN, cellulose fibers (such as viscose, rayon, and cotton), petroleum and coal tar pitch, and certain phenolic fibers. Synthesis process involves heat treatment, oxidative stabilization, carbonization and graphitization to achieve desired mechanical strength. It is well established in the literature that strength of fibers is the function of crystallinity and orientation, and by reducing defects in the fiber. The best way to achieve this is to start with a highly oriented precursor and then maintain the initial high orientation during the process of stabilization and carbonization through tension (http://tekim.undip.ac.id/staf/istadi/files/2009/05/topik51.pdf).

PAN has highly polar nitrile groups which cause strong dipole-dipole forces that act as cross-links, making the polymer soluble only in highly ionizing solvents, increasing its melting point, and making it more suitable as a carbon fiber precursor. In order to obtain PAN which results in such fiber properties, precursor ACN is required which is obtained from ammoxidation of propylene (petrochemical). The production of ACN accounts for approximately 70% of total cost, which is highly volatile with price currently ranging between $1,000 to 1,400/MT.

Recent advances have been made to produce ACN from glycerol (Olga, M., et al, Chem. Sus. Chem. (2008) 1, 511-513; Liebig, C., et al, Applied Catalysis B: Environmental (2013) 132-133, 170-182; Ulgen et. al. Catalysis Letters. 2009, 131: 122-128; Ulgen et. al. Applied catalysis A. General 400 (2011), 34-38), which can be sourced as a byproduct from biodiesel plants. While glycerol is available from subsidized biodiesel plants, for a long term solution, suitable renewable feed stocks and conversion process are needed.

It is known that propylene ammoxidation proceeds through an allylic intermediate acrolein. This ammoxidation was studied as early as 1963 by Adams et al over traditional Bismuth molybdate catalysts (Adams et al, Journal of Catalysis. (1963) 2, 63-68; http://wwwl.eere.energy.gov/vehiclesandfuels/pdfs/merit_review_2012/lightweight_materials/1m048_husman_2012_o.pdf). A renewed interest in acrolein ammoxidation has emerged due to high availability of glycerol as a byproduct from bio-diesel plants. Glycerol can be readily dehydrated to form acrolein; however bio-diesel plants are fast disappearing due to lack of subsidies. Thus, a constant source and pure glycerol is not available nor is the process economically atttractive, ACN produced from glycerol costs ~$2200/MT.

Figure 2:
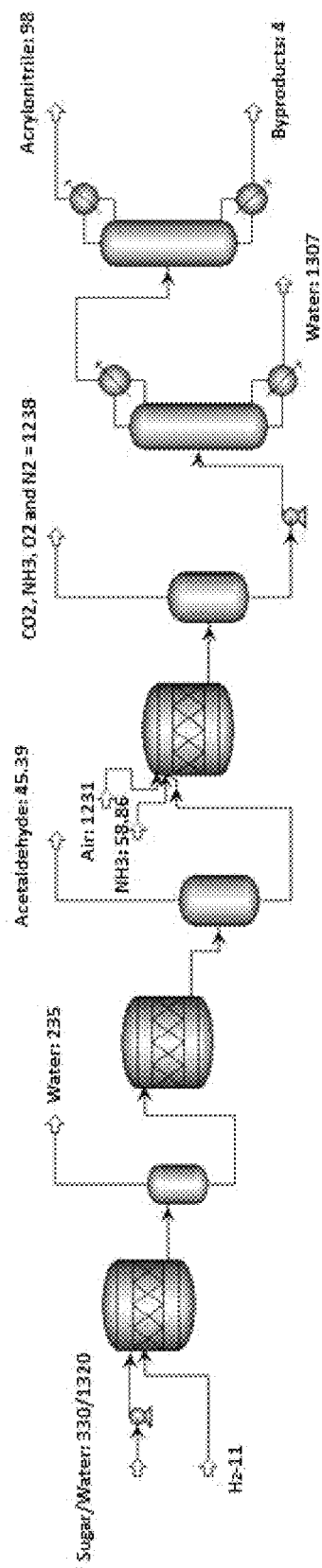
FIG. 2 shows the flow schematic of non-limiting aspects of the method disclosed herein for the process of producing acrylonitrile.

Disclosed herein is a catalyst and method that derive acrolein from a combination of diols and triols, such as propylene glycol and glycerol. The catalyst and method can be used with inexpensive starting materials, such as sugars, e.g. hemicellulose or cellulose sugars (cost around 5 to 40 cents/kg). The produced acrolein can in turn be converted to ACN. A schematic flow of the process to convert biomass to ACN is shown in FIG. 1 and FIG. 2.

A method of using sugars from sugars such as hemicellulose or cellulose derived sugars to produce polyols, e.g. ethylene glycol, propylene glycol, and glycerol, to form acrolein and acetaldehyde is disclosed herein. Such a method is desired because of its low carbon footprint and economic viability.

Also disclosed herein is a multifunctional catalyst capable of, in a single step, converting C5 and C6 sugars to ethylene glycol, propylene glycol, and glycerol. In one aspect, the, C5 and C6 sugars are hemicellulose or cellulose derived C5 and C6 sugars from biomass.

a. Catalyst Composition

The catalyst disclosed herein can convert glycerol and propylene glycol ($C_3$ polyols) to acrolein, while simultaneously converting ethylene glycol ($C_2$ diol) to acetaldehyde. Such product mixture is desired because acetaldehyde can easily be separated from the acrolein by use of low energy distillation or flash vaporization. ACN can then be produced by ammoxidizing acrolein in presence of ammonia and oxygen (air).

Disclosed herein is a catalyst composition for converting propylene glycol and glycerol to acrolein comprising a catalyst having the formula:

$$M1M2_xM3_yO_z$$

wherein M1 is a metal promoting dehydrogenation and C—O cleavage, wherein M2 is a metal with acid sites promoting dehydration, wherein M3 is an amphoteric catalyst support, with acid and base sites, promoting both dehydration and dehydrogenation in conjunction with M1, wherein x is a molar ratio from about 0.25 to about 4, wherein y is a molar ratio from about 0.25 to about 4, wherein z is the total amount of oxygen bound to M1, M2, and M3, and corresponds to the sum of the oxidation states of M1, M2, and M3.

In the formula $M1M2_xM3_yO_z$, the metals M1, M2, and M3 are different metals.

The catalyst composition comprises metals that advantageously dehydrogenate (M1, M3) and then dehydrate (M2, M3) diols or triols, such as, for example, ethylene glycol, propylene glycol, and glycerol. As such the catalyst composition can convert ethylene glycol into acetaldehyde and convert propylene glycol and glycerol to acrolein. These conversions are desired as acetaldehyde can easily be separated from acrolein due to their different boiling temperatures.

M1 is a metal promoting dehydrogenation and C—O cleavage in molecules, such as, for example, dehydrogenation and C—O cleavage in diols and triols, such as, for example, ethylene glycol, propylene glycol, and glycerol. In one aspect, M1 is selected from the group consisting of Cu, Zn, and Sn. For example, M1 can be Cu. In another example, M1 can be Zn. In yet another example, M1 can be Sn.

M2 is a metal with acid sites promoting dehydration in molecules, such as, for example, dehydration in diols and triols, such as, for example, ethylene glycol, propylene glycol, and glycerol. In one aspect, M2 is selected from the group consisting of W, Fe, P, and a zeolite. For example, M2 can be W. In another example, M2 can be Fe. In yet another example, M2 can be P. In yet another example, M2 can be a zeolite.

M3 is an amphoteric catalyst support, with acid and base sites, promoting both dehydration and dehydrogenation in conjunction with M1 in molecules, such as, for example, dehydration and dehydrogenation in conjunction with M1 in diols or triols, such as, for example, ethylene glycol, propylene glycol, and glycerol. In one aspect, M3 is selected from the group consisting of Zr, Al, Si, Mg, Ti, La, and Ce. For example, M3 can be Zr. In another example, M3 can be Al. In yet another example, M3 can be Si. In yet another example, M3 can be Mg. In yet another example, M3 can be a Ti. In yet another example, M3 can be a La. In yet another example, M3 can be a Ce. Selection of M3 can be is dictated by the support's stability in steam phase conditions. For example, alumina can be modified using silica as described by Ravenelle et al (Ravenelle, R. M., et al, ACS Catalysis (2011) 1, 552-561; Ravenelle, R. M., et al, ChemCatChem (2012) 4, 492-494).

In one aspect, M1 can be Cu, M2, can be W, and M3 is selected from the group consisting of Zr, Al, Si, Mg, Ti, La, and Ce. In another aspect, M1 can be Cu, M2, can be selected from the group consisting of W, Fe, P, and a zeolite, and M3 can be Zr. In yet another aspect, M1 can be selected from the group consisting of Cu, Zn, and Sn, M2, can be W, and M3 can be Zr.

In one aspect, M1 can be Cu, M2, can be selected from the group consisting of W, Fe, P, and a zeolite, and M3 can be selected from the group consisting of Zr, Al, Si, Mg, Ti, La, and Ce. In another aspect, M1 can be selected from the group consisting of Cu, Zn, and Sn, M2 can be W, and M3 can be selected from the group consisting of Zr, Al, Si, Mg, Ti, La, and Ce. In yet another aspect, M1 can be selected from the group consisting of Cu, Zn, and Sn, M2 can be selected from the group consisting of W, Fe, P, and a zeolite, and M3 can be Zr.

In one aspect, x is a molar ratio from about 0.25 to about 4. In another aspect, x is a molar ratio from about 0.8 to about 4. In yet another aspect, x is a molar ratio from about 1.8 to about 4. In yet another aspect, x is a molar ratio from about 0.25 to about 3. In yet another aspect, x is a molar ratio from about 0.25 to about 2.2. In yet another aspect, x is a molar ratio from about 0.8 to about 2.2.

In one aspect, y is a molar ratio from about 0.25 to about 4. In another aspect, y is a molar ratio from about 0.8 to about 4. In yet another aspect, y is a molar ratio from about 1.8 to about 4. In yet another aspect, y is a molar ratio from about 0.25 to about 3. In yet another aspect, y is a molar ratio from about 0.25 to about 2.2. In yet another aspect, y is a molar ratio from about 0.8 to about 2.2.

In one aspect, z is the total amount of oxygen bound to M1, M2, and M3, and corresponds to the sum of the oxidation states of M1, M2, and M3. It is known in the art how to determine z based on the oxidation state of M1. M2, and M3.

In one aspect, M1 and M2, together with their respective amounts of oxygen based on oxidation state, are present in an amount from 1 wt to 40 wt % of the catalyst wherein the support M3 provides the balance wt %. In another aspect, M1 and M2, together with their respective amounts of oxygen based on oxidation state, are present in an amount from 1 wt % to 30 wt % of the catalyst wherein the support M3 provides the balance wt %. M1 and M2, together with their respective amounts of oxygen based on oxidation state, are present in an amount from 1 wt % to 20 wt % of the catalyst wherein the support M3 provides the balance wt %. M1 and M2, together with their respective amounts of oxygen based on oxidation state, are present in an amount from 5 wt to 20 wt % of the catalyst wherein the support M3 provides the balance wt %.

In one aspect, the catalyst has the formula $CuOWO_3ZrO_2$. In another aspect, the catalyst has the formula $CuOWO_3TiO_2$. In another aspect, the catalyst has the formula $CuOWO_3SiO_2$.

The catalyst can be produced using co-impregnation of metal salts on acid supports, followed by calcination, which is typically performed at a temperature between 300° C. to 600° C., such as about 450° C.

b. Method

The method disclosed herein reduces the steps needed to convert biomass to useful products such as ethylene glycol, propylene glycol, glycerol, acrolein, and acrylonitrile. As a result, the method further reduces the greenhouse gas emission as compared to previously known processes.

I. Production of Ethylene Glycol, Propylene Glycol, and Glycerol

Disclosed herein is a method that converts sugars, such as C5 and/or C6 sugars to ethylene glycol, propylene glycol, and glycerol.

Disclosed herein is a method comprising the step of: a) in a single step, converting C5 and/or C6 sugars to a first product comprising ethylene glycol, propylene glycol, and glycerol in the presence of a multifunctional catalyst.

In one aspect, the C5 and/or C6 sugars can be C5 and/or C6 hemicellulose and cellulose derived sugars. The C5 and/or C6 sugars or C5 and/or C6 hemicellulose and cellulose derived sugars can be produced from any type of biomass. Biomass is known in the art and is biological material derived from living, or recently living organisms. The process of producing C5 and/or C6 sugars or C5 and/or C6 hemicellulose and cellulose derived sugars from biomass is known in the art.

Figure 3:
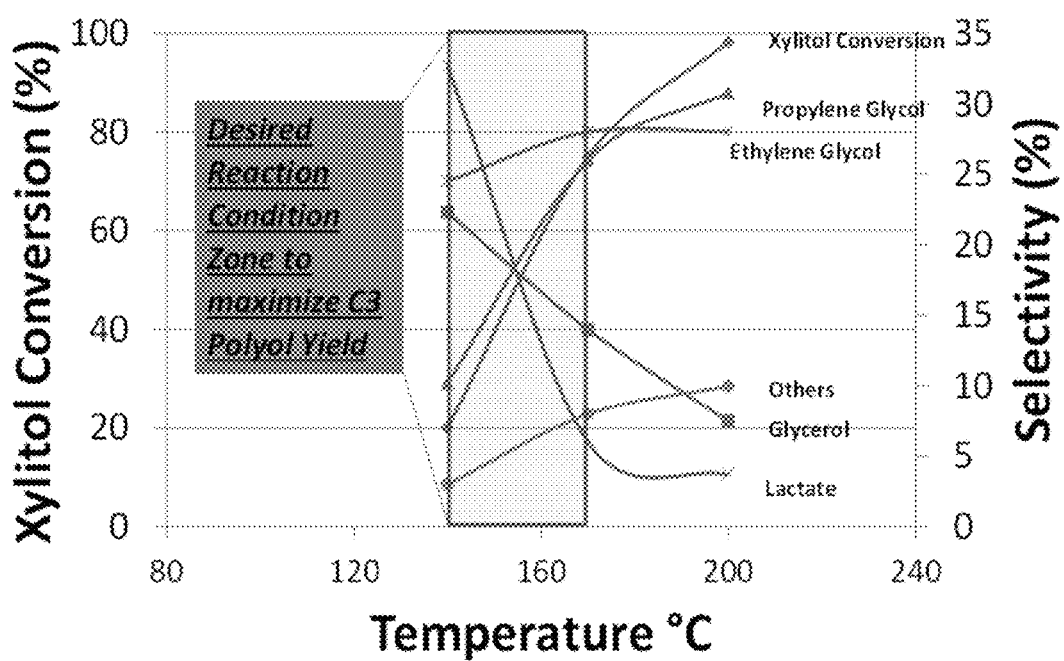
FIG. 3 shows the influence of reaction condition for product distribution of the conversion of sugars to $C_2$, $C_3$ diols and triols, such as ethylene glycol, propylene glycol and glycerol.

For example, hot water extraction of hemicellulose from biomass is a self-catalytic process, autohydrolysis. This mechanism of hydrolysis lies in cleavage of O-acetyl and uronic acid substitutions that result in the formation of acetic and other organic acids, which makes it possible for further hydrolysis of polysaccharides to oligomers and monomers (Niemelä, K., et al, 1999. Characterization of pulping liquors, in: Analytical Methods in Wood Chemistry, Pulping and Papermaking. Springer-Verlag, Berlin). The main degradation pathways of hemicelluloses under acidic conditions liberate xylose, mannose, galactose, glucose, and acetic acid. The temperature and pressure and incubation time can be controlled to avoid the degradation of xylan to furfural (Palmqvist, E., et al, Bioresource Technology (2000) 74, 25-33) and of hexose to 5-hydroxymethylfurfural (HMF). FIG. 3 shows the conversion of xylitol to ethylene glycol, propylene glycol, and glycerol and other products.

The multifunctional catalyst is capable of converting the C5 and/or C6 sugars in a single step to diols and triols. Thus, the there is no need for separation steps or the production of intermediates to produce the diols and triols. Such a method saves both time and resources as compared to methods requiring multiple steps.

The conversion of the C5 and/or C6 sugars to a first product comprising ethylene glycol, propylene glycol, and glycerol in the presence of a multifunctional catalyst is performed in a solvent, such as, for example, water. In one aspect, the method further comprises the step of separating at least a portion of the water from the first product. In one aspect, the concentration of the first product is from about 10 wt % to about 40 wt %, such as, for example, from about 20 wt % to about 35 wt %, in the water after a portion of the water has been separated from the first product.

In one aspect, the multifunctional catalyst comprises one or more metals selected from the group consisting of Cu, Zn, Sn, Ni, Pt, Pd, Ru, and Re, and a support. In one aspect, the support is selected from the group consisting of $Al_2O_3$, $SiO_2$, Carbon, $TiO_2$, and MgO.

Figure 5:
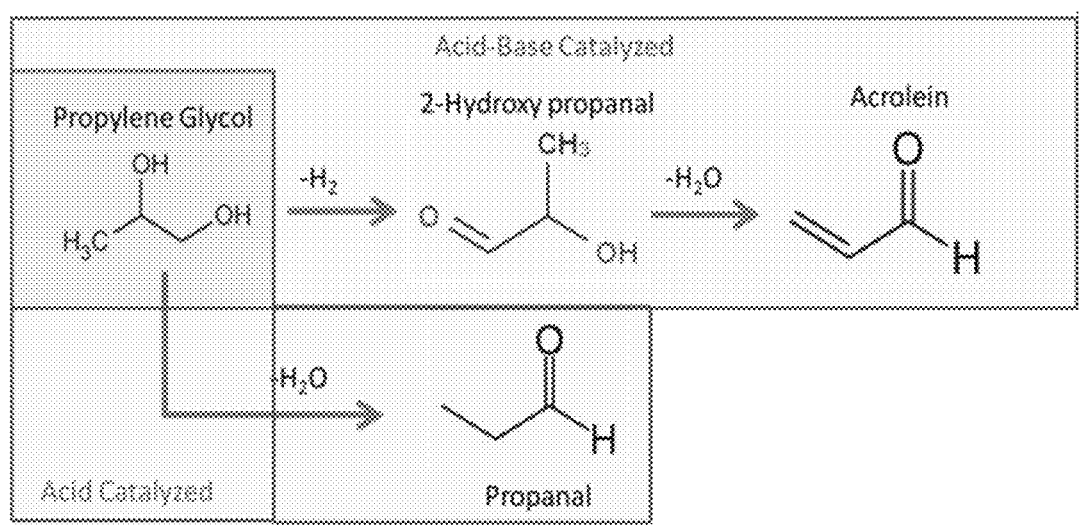
FIG. 5 shows the catalytic reaction pathway for propylene glycol to acrolein and propanal.

In one aspect, the multifunctional catalyst comprises Ni and Cu and the support comprises $Al_2O_3$. The selectivity of various products can be altered by altering the amount of Ni and Cu and the support comprises $Al_2O_3$ as shown in FIG. 5. Cu can serve for C—O cleavage (Dasari, M. A., et al, Applied Catalysis A: General (2005) 281 225-23), Ni for C—C cleavage and hydrogenation and Lewis acid support ($Al_2O_3$) for C—C cleavage and dehydration. Lower amount of copper and nickel over Lewis acid support favors formation of C3 polyols (less cracking), medium nickel and copper favors C2 diols (slight enhanced cracking), whereas even higher Ni and Cu favors formation of alcohols (high degree of both C—C and C—O cleavage with hydrogenation).

In one aspect, the multifunctional catalyst comprises less than 10 wt % of Cu and less than 20 wt % of Ni, and the remainder being $Al_2O_3$. In another aspect, the multifunctional catalyst comprises from about 1 wt % to about 9 wt % of Cu and from about 1 wt % to about 19 wt % of Ni, and the remainder being $Al_2O_3$. Conventional nickel catalyst supported on γ-alumina are unstable due to structural loss under hydrothermal conditions (Ravenelle, R. M., et al, ACS Catalysis (2011) 1, 552-561) making metal sites unavailable. Effect of metal on support structure (Ravenelle, R. M., et al, ChemCatChem (2012) 4, 492-494), role of co-adsorbed water on support during C2 and C3 polyol reactions (Copeland, J. R., et al, Langmuir (2013) 29, 581-593) and addition of silica to increase thermal stability has been studied. Furthermore, addition of Cu to Ni catalyst on such supports has known to increase their integrity under hydrothermal conditions (U.S. Pat. No. 5,977,013).

In one aspect, the multifunctional catalyst can further comprise Pt, such as less than 0.5 wt % of Pt, less than 0.3 wt % of Pt, for example, about 0.1 wt % of Pt. The Pt facilitates long term activity and the ability of the catalyst to regenerate.

In one aspect, the first product comprises from about 10 wt % to about 40 wt % of ethylene glycol, from about 10 wt % to about 50 wt % of propylene glycol, and from about 10 wt % to about 50 wt % of glycerol. In one aspect, the first product comprises from about 20 wt % to about 35 wt % of ethylene glycol, from about 30 wt % to about 45 wt % of propylene glycol, and from about 30 wt % to about 45 wt % of glycerol.

In one aspect, at least 95 wt % of the C5 and/or C6 sugars in step a) are converted to the first product comprising ethylene glycol, propylene glycol, and glycerol. In another aspect, at least 98 wt % of the C5 and/or C6 sugars in step a) are converted to the first product comprising ethylene glycol, propylene glycol, and glycerol. In yet another aspect, at least 99 wt % of the C5 and/or C6 sugars in step a) are converted to the first product comprising ethylene glycol, propylene glycol, and glycerol.

In one aspect, the step of converting C5 and/or C6 sugars to a first product comprising ethylene glycol, propylene glycol, and glycerol in the presence of a multifunctional catalyst is performed under mild conditions. For example, the step of converting C5 and/or C6 sugars to a first product comprising ethylene glycol, propylene glycol, and glycerol in the presence of a multifunctional catalyst is performed under mild conditions can be performed at a temperature from about 130° C. to about 200° C., and at a pressure from about 400 psig to about 1000 psig in presence of hydrogen. In another example, the step of converting C5 and/or C6 sugars to a first product comprising ethylene glycol, propylene glycol, and glycerol in the presence of a multifunctional catalyst is performed under mild conditions can be performed at a temperature from about 130° C. to about 180° C., and at a pressure from about 400 psig to about 800 psig in presence of hydrogen.

The use of mild conditions during the conversion of the C5 and/or C6 sugars to the first product allows the multifunctional catalyst to be active for a longer period of time as compared to the same catalyst used under harsher conditions. Desired conversion rates, for example above 95 wt %, of the C5 and/or C6 sugars can be achieved by the method for at least 100 hrs, such as, for example, from 100 hrs to 500 hrs.

In one aspect, the method can further comprise the step of contacting the first product comprising ethylene glycol, propylene glycol, and glycerol with the catalyst composition disclosed herein, thereby producing a second product comprising acrolein and acetaldehyde. In one aspect, the method can further comprise the steps of separating at least a portion of the acetaldehyde from the second product; and converting at least a portion of the acrolein in the second product to acrylonitrile.

In one aspect, the method is performed on an industrial scale. For example, the method can produce at least 30 g/l/hr. such as, for example, at least 45 g/l/hr, of the first product per hour. In another example, the method can produce from about 30 g/l/hr to about 200 g/l/hr of the first product per hour.

Figure 4:
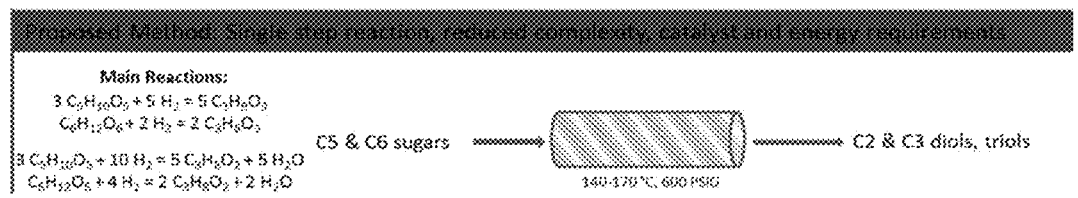
FIG. 4 shows the single step process for hydrocracking reaction for converting sugars to $C_2$, $C_3$ diols and triols, such as ethylene glycol, propylene glycol and glycerol.

A schematic flow of the method disclosed herein is shown in FIG. 4.

II. Production of Acrolein and Acetaldehyde

The catalyst disclosed herein can be used to convert ethylene glycol to acetaldehyde and convert propylene glycol and glycerol to acrolein.

Disclosed herein is a method comprising the step of: a) contacting a first product comprising ethylene glycol, propylene glycol, and glycerol with the catalyst disclosed herein, thereby producing a second product comprising acrolein and acetaldehyde.

In one aspect, the method further comprises the steps of: b) separating at least a portion of the acetaldehyde from the second product; and c) following step b) converting at least a portion of the acrolein in the second product to acrylonitrile.

In it known in the art how to convert acrolein to acrylonitrile. For example, acrylonitrile can be produced from acrolein ammoxidation, which is a simultaneous oxidation of an organic group (R) and ammonia, such a mutual reaction results in oxidative condensation product to form R'—CN molecule such as acrylonitrile. Such a reaction is not possible if a separate oxidation of R and ammonia are conducted. Hadley et al (Hadley, D. J., Chemy Ind. (1961) 238) has proposed a two-step reaction mechanism, dehydration due to reaction with ammonia (fast step), and oxidative-dehydration of intermediate (rate limiting step). Therefore, as partial pressure of oxygen increases, the higher surface concentration of oxygen on catalyst leads to higher selectivity to acrylonitrile and acetonitrile (by-product) with net decrease in $CO_2$.

In one aspect, step a) is performed at atmospheric pressure.

In one aspect, the first product is present in a solvent, such as, for example, water.

In one aspect, the second product is present in diluent, such as, for example, water. In one aspect, the method can further comprise removing at least a portion of the dilutent, thereby concentrating the second product.

In one aspect, the second product further comprises propanal, which can be produced from the first product by the catalyst disclosed herein. The mechanism for the conversion of propylene glycol to acrolein and propanal with various types of catalysts is shown in FIG. 5.

The catalyst disclosed herein typically has three different sites, acid as well as base for dehydration of glycerol, base catalyzed sites for dehydration of propylene glycol to propylene oxide and Cu promoted neutral catalysts for dehydrogenation/dehydration. Thus in one aspect, the catalyst used in the method is neither too acidic nor too basic. Therefore, supports that show have acid-base properties are useful to obtain acrolein from propylene glycol via the reaction pathway shown above, which involves dehydrogenation followed by dehydration.

Accordingly, also disclosed herein is a method comprising the step of: a) contacting propylene glycol with a catalyst composition, thereby producing acrolein. In one aspect, the catalyst composition is a catalyst composition disclosed herein. For example, the catalyst composition can comprise a catalyst having the formula: $M1M2_xM3_yO_z$. In another example, the catalyst composition can comprise a catalyst having the formula $CuOWO_3ZrO_2$, or $CuOWO_3TiO_2$, or $CuOWO_3SiO_2$.

The high boiling point molecules; propylene glycol (188° C.), ethylene glycol (197.3° C.) and glycerol (290° C.) can be difficult to separate. However when ethylene glycol is converted to acetaldehyde (20.2° C.) and propylene glycol and glycerol to acrolein (53° C.), respectively, the low boiling point of these molecules facilitates easy separation via a low energy distillation or flash vaporization.

In one aspect, from about 10 wt % to about 90 wt % of the propylene glycol and glycerol in the first product are converted to acrolein. For example, from about 30 wt % to about 90 wt % of the propylene glycol and glycerol in the first product can be converted to acrolein. In another example, from about 50 wt % to about 90 wt % of the propylene glycol and glycerol in the first product can be converted to acrolein. In yet another example, from about 50 wt % to about 80 wt % of the propylene glycol and glycerol in the first product can be converted to acrolein.

In one aspect, the second product comprises from about 20 wt % to about 75 wt % of acrolein. For example, second product comprises from about 50 wt % to about 75 wt % of acrolein. In another example, second product comprises from about 55 wt % to about 70 wt % of acrolein. The second product can be present in a diluent, which is not a part of the second product.

In one aspect, the first product is produced from C5 and/or C6 sugars in a single step using a multifunctional catalyst, as described elsewhere herein. In one aspect, the C5 and/or C6 sugars can be C5 and/or C6 hemicellulose and cellulose derived sugars. The process of producing C5 and/or C6 sugars or C5 and/or C6 hemicellulose and cellulose derived sugars from biomass is also described herein.

In one aspect, the method can be performed for at least 12 hours without losing more than 10% of the conversion rate of the first product to the second product. In one aspect, the method can be performed for at least 24 hours without losing more than 10% of the conversion rate of the first product to the second product. In one aspect, the method can be performed from about 12 hours to about 50 hours without losing more than 10% of the conversion rate of the first product to the second product.

In one aspect, the method is performed on an industrial scale. For example, the method can produce at least 75 g/l of the second product per hour.

Figure 6:
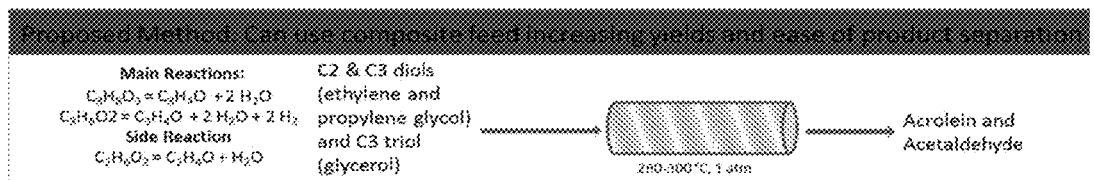
FIG. 6 shows process for producing acrolein an acetaldehyde from $C_2$, $C_3$ diols and triols, such as ethylene glycol, propylene glycol and glycerol.

A schematic flow of the method disclosed herein is shown in FIG. 6.

3. Aspects

In view of the disclosure herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: A catalyst composition for converting propylene glycol and glycerol to acrolein comprising a catalyst having the formula:

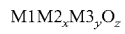

wherein M1 is a metal promoting dehydrogenation and C—O cleavage,
wherein M2 is a metal with acid sites promoting dehydration,
wherein M3 is an amphoteric catalyst support, with acid and base sites, promoting both dehydration and dehydrogenation in conjunction with M1,
wherein x is a molar ratio from about 0.25 to about 4,
wherein y is a molar ratio from about 0.25 to about 4,
wherein z is the total amount of oxygen bound to M1, M2, and M3, and corresponds to the sum of the oxidation states of M1, M2, and M3.

Aspect 2: The catalyst composition of aspect 1, wherein M1 is selected from the group consisting of Cu, Zn, and Sn.

Aspect 3: The catalyst composition of aspects 1 or 2, wherein M2 is selected from the group consisting of W, Fe, P, and a zeolite.

Aspect 4: The catalyst composition of any one of aspects 1-3, wherein M3 is selected from the group consisting of Zr, Al, Si, Mg, Ti, La, and Ce.

Aspect 5: The catalyst composition of any one of aspects 1-4, wherein x is from about 0.8 to about 2.2.

Aspect 6: The catalyst composition of any one of aspects 1-5, wherein y is from about 0.8 to about 2.2.

Aspect 7: The catalyst composition of any one of aspects 1-6 wherein M1 is Cu.

Aspect 8: The catalyst composition of any one of aspects 1-7, wherein M2 is W.

Aspect 9: The catalyst composition of any one of aspects 1-8, wherein M3 is Zr.

Aspect 10: The catalyst composition of any one of aspects 1-9, wherein the catalyst has the formula $CuOWO_3ZrO_2$, or $CuOWO_3TiO_2$, or $CuOWO_3SiO_2$.

Aspect 11: A method comprising the step of: a) contacting a first product comprising ethylene glycol, propylene glycol, and glycerol with the catalyst composition of any one of aspects 1-10, thereby producing a second product comprising acrolein and acetaldehyde.

Aspect 12: The method of aspect 11, wherein the method further comprises the steps of: b) separating at least a portion of the acetaldehyde from the second product; and c) following step b) converting at least a portion of the acrolein in the second product to acrylonitrile.

Aspect 13: The method of aspects 11 or 12, wherein the first product is produced from C5 and/or C6 sugars in a single step using a multifunctional catalyst.

Aspect 14: The method of aspect 13, wherein the C5 and/or C6 sugars is C5 and/or C6 hemicellulose and cellulose derived sugars.

Aspect 15: The method of any one of aspects 11-14, wherein from about 10 wt % to about 90 wt % of the propylene glycol and glycerol in the first product are converted to acrolein.

Aspect 16: The method of any one of aspects 11-15, wherein the second product comprises from about 20 wt % to about 75 wt % of acrolein.

Aspect 17: The method of any one of aspects 13-16, wherein the multifunctional catalyst comprises one or more metals selected from the group consisting of Cu, Zn, Sn, Ni, Pt, Pd, Ru, and Re, and a support.

Aspect 18: The method of aspect 17, wherein the support is selected from the group consisting of $Al_2O_3$, $SiO_2$, carbon, $TiO_2$, and MgO.

Aspect 19: The method of any one of aspects 11-18, wherein step a) is performed at atmospheric pressure.

Aspect 20: A method comprising the step of: a) in a single step, converting C5 and/or C6 sugars to a first product comprising ethylene glycol, propylene glycol, and glycerol in the presence of a multifunctional catalyst.

Aspect 21: The method of aspect 20, wherein the multifunctional catalyst comprises one or more metals selected from the group consisting of Cu, Zn, Sn, Ni, Pt, Pd, Ru, and Re, and a support.

Aspect 22: The method of aspect 21, wherein the support is selected from the group consisting of $Al_2O_3$, $SiO_2$, Carbon, $TiO_2$, and MgO.

Aspect 23: The method of any one of aspects 20-22, wherein the method further comprises the step of separating water from the first product.

Aspect 24: The method of any one of aspects 20-23, wherein the method further comprises the step of contacting the first product comprising ethylene glycol, propylene glycol, and glycerol with the catalyst composition of any one of aspects 1-10, thereby producing a second product comprising acrolein and acetaldehyde.

Aspect 25: The method of aspect 24, wherein method further comprises the steps of separating at least a portion of the acetaldehyde from the second product; and converting at least a portion of the acrolein in the second product to acrylonitrile.

Aspect 26: The method of any one of aspects 20-25, wherein the C5 and/or C6 sugars is C5 and/or C6 hemicellulose and cellulose derived sugars.

Aspect 27: The method of any one of aspects 20-26, wherein from about 70 wt % to about 100 wt % of the C5 and/or C6 sugars in step a) are converted to the first product.

Aspect 28: The method of any one of aspects 20-27, wherein step a) is performed at a temperature from about 130° C. to about 200° C., and at a pressure from about 400 psig to about 1000 psig in presence of Hydrogen.

Aspect 29: A method comprising the step of: a) contacting propylene glycol with a catalyst composition, thereby producing acrolein.

Aspect 30: The method of aspect 29, wherein the catalyst composition is the catalyst composition of any one of aspects 1-10.

Aspect 31: The method of aspect 30, wherein M1 is selected from the group consisting of Cu, Zn, and Sn, wherein M2 is selected from the group consisting of W, Fe, P, and a zeolite, wherein M3 is selected from the group consisting of Zr, Al, Si, Mg, Ti, La, and Ce.

Aspect 32: The method of aspect 30, wherein the catalyst has the formula $CuOWO_3ZrO_2$, or $CuOWO_3TiO_2$, or $CuOWO_3SiO_2$.

Aspect 33: The method of any one of aspects 29-32, wherein step a) is performed at atmospheric pressure.

Aspect 34: The method of any one of aspects 29-33, wherein from about 10 wt % to about 90 wt % of the propylene glycol is converted to acrolein.

Aspect 35: The method of one of aspects 11-19, wherein M1 is selected from the group consisting of Cu, Zn, and Sn, wherein M2 is selected from the group consisting of W, Fe, P, and a zeolite, and wherein M3 is selected from the group consisting of Zr, Al, Si, Mg, Ti, La, and Ce.

Aspect 36: The method of one of aspects 11-19, wherein the catalyst has the formula $CuOWO_3ZrO_2$, or $CuOWO_3TiO_2$, or $CuOWO_3SiO_2$.

4. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. The Examples are provided herein to illustrate the invention, and should not be construed as limiting the invention in any way.

1. Experimental Parameters and Testing of Catalysts

Preparation of $CuOWO_3ZrO_2$: A Tungsten Hexachloride Solution in Ethanol (0.056 g/ml of solution) was prepared. It is noted that other tungsten salts may also be used in this process. $ZrO_2$ was obtained from Alfa Aesar (catalog number 43815) with a surface area of 90 $m^2$/g. This was crushed to the required size (−20, +35 mesh) and the required amount of Tungsten Hexachloride solution for 20 wt % resultant $WO_3$ was added (61.6 ml, the salt has poor solubility and thus excess solution was added), along with 10 ml of water to achieve better dissolution and retrieve traces of salt. The solution was impregnated on crushed $ZrO_2$ and allowed to dry at room temperature for 4 to 5 hrs. A second solution of Copper nitrate hexahydrate (0.043 g/ml) was prepared; this solution was impregnated on top of previously obtained tungsten hexacholride on $ZrO_2$ sample. The sample was allowed to dry at 100° C. overnight. Dried sample was calcined in a high temperature oven under air using following program, room temperature to 100° C. at 1° C./min and held at 110° C. for 1 hour, then 110° C. to 450° C. at 5° C./min, and held at 450° C. for 3 hours.

$CuOWO_3ZrO_2$ was tested as a catalyst for the conversion of propylene glycol to acrolein. 20 wt % propylene glycol was used as a reactant and a co flow of $N_2$ of 50 SCCM This reaction was conducted in fixed bed reactor. The catalyst was loaded in the center of heated zone, with inert low surface glass beads as filler material on top and bottom of reactor. At the bottom of reactor a 5 micron metal grid was used as support for catalyst material. At the inlet of reactor, feed was preheated to desired temperature. The gas phase reaction was studied at 280° C. and 1 atm using $WO_3/ZrO_2$ and $CuO/WO_3/ZrO_2$ as dehydrating/dehydrogenating catalysts, with a flow of 5 g/hr and 5 grams of each catalyst for a WHSV of 1/hr. The gas effluent was connected to an online GC-FID which was pre-calibrated for acrolein and feed component. The presence of acrolein in the product was confirmed using a standard on GC-FID and GC-MS.

TABLE 1

| | Catalyst | |
| --- | --- | --- |
| | $WO_3/ZrO_2$ | $CuO/WO_3/ZrO_2$ |
| Temperature - ° C. | 280 | 280 |
| Pressure - psig | 14.7 | 14.7 |
| Propylene glycol conversion - % | 100% | 100% |
| Selectivity to Acrolein - % | 35% | 42% |

As shown in Table 1, a CuO/WO$_3$/ZrO$_2$ catalyst has an increased selectivity for the production of acrolein from propylene glycol as compared to a WO$_3$/ZrO$_2$ catalyst.

2. Experimental Parameters and Testing of Catalysts

Catalyst for conversion of sugar to glycols was prepared using following methods and materials: catalyst 1) 0.1 wt % Pt/10 wt % Ni/Al$_2$O$_3$—Nickel Hexhydrate salt was dissolved in water for a resultant concentration of 0.04036 grams of Ni/gram of solution. 0.25 grams of Tetraamineplatinum (II) nitrate solution was added to this solution. Commercial Alumina obtained from Alfa Aesar (catalog number 43855) with a surface area of 220 m$^2$/g and pore size of 70 Å was used. This support was crushed and sieved to (−20, +35 mesh). Salt solution was impregnated on the solid catalyst support to obtain desired metal concentration ranging from 1 to 20 wt % of metal (Ni) and 0.1 wt % of Pt. The sample was allowed to dry at room temperature for 3 hrs and then at 60° C. on a hot plate overnight. Dried sample was calcined under air in a conventional high temperature oven using the following program. Room temperature to 100° C. in 1.5 hours, held at 100° C. for 1 hour, 100 to 120° C. in 30 minutes, held at 120° C. for 1 hour, 120 to 450° C. at 10° C./min and held at 450° C. for 3 hours.

Catalyst 2): For a 0.1 wt % Pt/10 wt % Ni/10 wt % Cu/Al$_2$O$_3$ catalyst—Nickel Hexhydrate salt was dissolved in water for a resultant concentration of 0.04036 grams of Ni/gram of solution. 0.25 grams of Tetraamineplatinum (II) nitrate solution was added to this solution. Commercial Alumina obtained from Alfa Aesar (catalog number 43855) with a surface area of 220 m2/g and pore size of 70 Å was used. This support was crushed and sieved to (−20, +35 mesh). Salt solution was impregnated on the solid catalyst support to obtain desired metal concentration ranging from 1 to 20 wt % of metal (Ni) and 0.1 wt % of Pt. The sample was allowed to dry at room temperature for 3 hrs and then at 60° C. on a hot plate overnight. Similarly, copper solution was prepared using Copper nitrate hexahydrate in water for a concentration of (0.0789 grams of copper/gram of solution). This solution was impregnated on top of the obtained sample, dried at room temp for 3 hours and then at 60° C. overnight.

Figure 10:
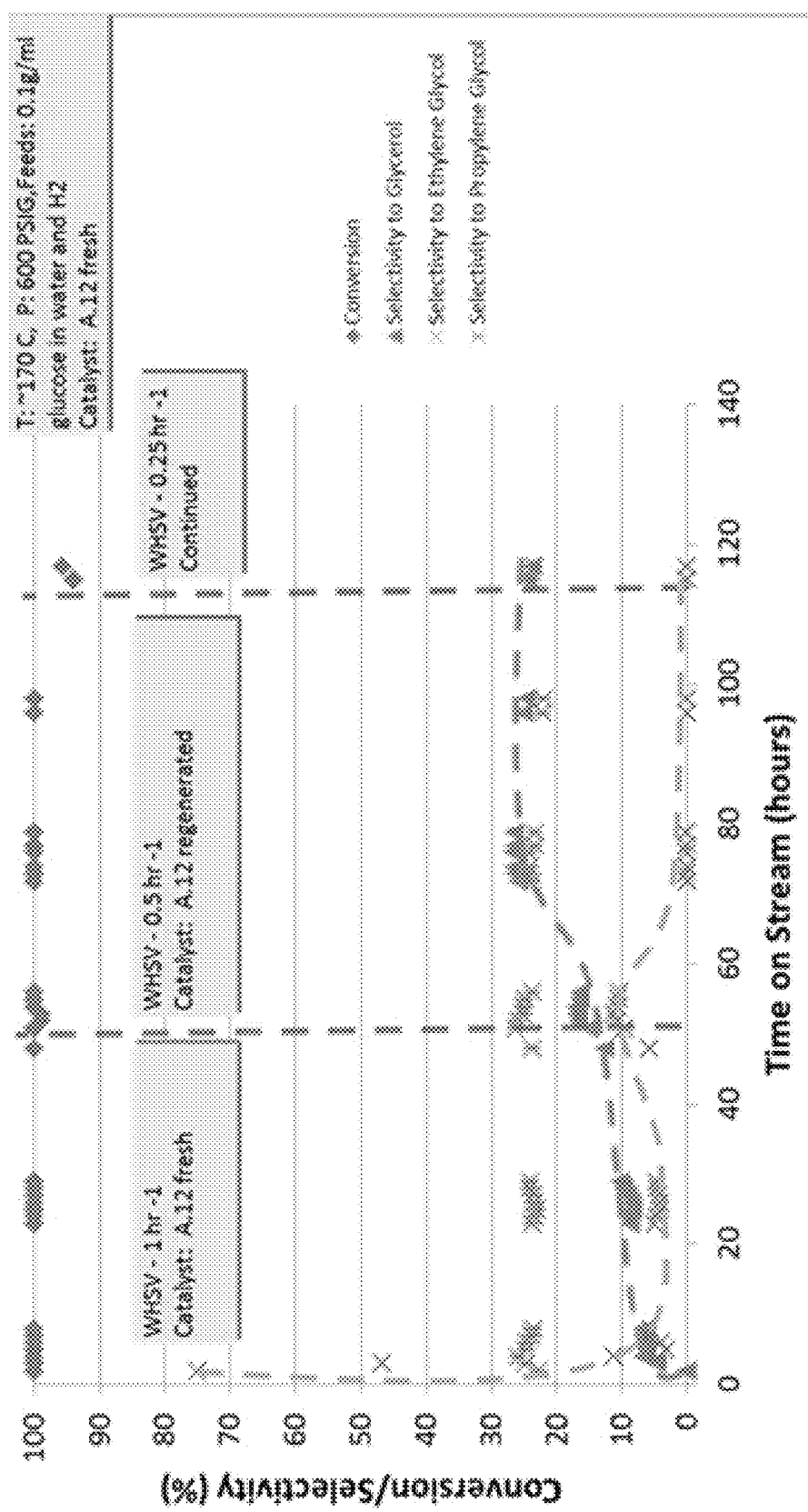
FIG. 10 shows the stability as a function of time and reaction conditions for catalyst 3).
Figure 11:
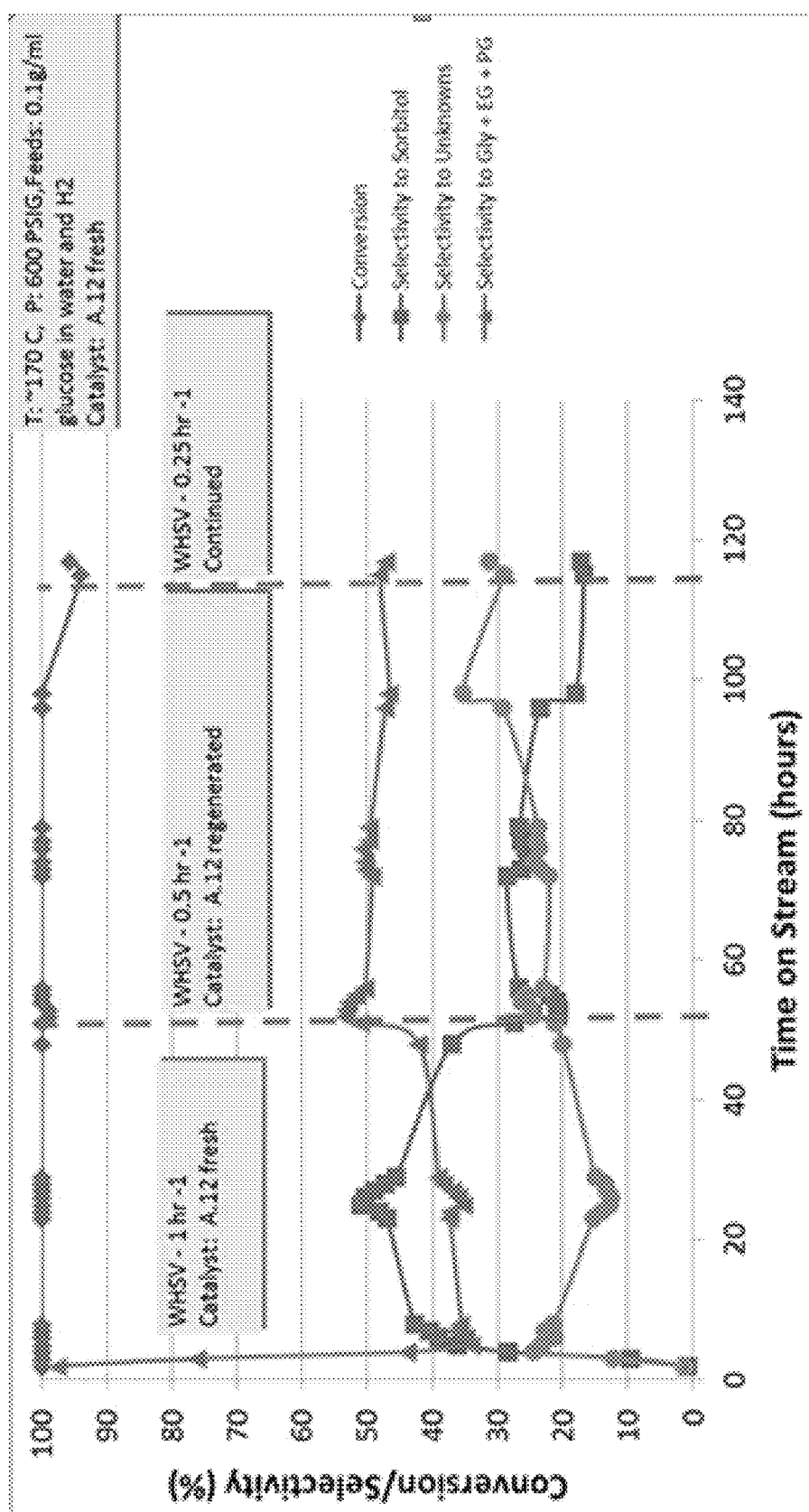
FIG. 11 shows the selectivity as a function of time and reaction conditions for catalyst 3).

Catalyst 3): For a 0.1 wt % Pt/10 wt % Ni/10 wt % Cu/Al$_2$O$_3$ catalyst (Catalyst A.12, as shown in FIGS. 10 and 11)—Copper Nitrate trihydrate salt was dissolved in water for a resultant concentration of 0.078 grams of Cu/gram of solution. Commercial Alumina obtained from Alfa Aesar (catalog number 43855) with a surface area of 220 m$^2$/g and pore size of 70 Å was used. This support was crushed and sieved to (−20, +35 mesh). Salt solution was impregnated on the solid catalyst support to obtain desired metal concentration ranging from 1 to 20 wt % of metal (Cu). The sample was allowed to dry at room temperature for 3 hrs and then at 60° C. on a hot plate overnight. Dried sample was calcined under air in a conventional high temperature oven using the following program. The temperature was increased from room temperature to 60° C. at a rate of 12° C./min and held at 60° C. for 5 minutes. The temperature was increased from 60° C. to 100° C. at 14° C./min, and held at 100° C. for 1 hour. The temperature was then increased from 100° C. to 120° C. at 7° C./min, and held at 120° C. for 1.5 hours. The temperature was then increased from 120° C. to 450° C. at 10° C./min and held at 450° C. for 3 hours. Following calcination, the catalyst sample was allowed to cool down to room temperature. A second metal impregnation was then conducted, Nickel solution was prepared using nickel nitrate hexahydrate in water for a concentration of (0.05 grams of nickel/gram of solution). 0.25 grams of Tetraamineplatinum (II) nitrate solution was added to this solution. Resultant salt solution was impregnated on the calcined sample to obtain desired metal concentration ranging from 1 to 20 wt % of metal (Ni) and 0.1 wt % of Pt. Sample was dried at room temp for 3 hours and then at 60° C. overnight. The dried sample was calcined under air in a conventional high temperature oven using the following program. The temperature was increased from room temperature to 60° C. at a rate of 12° C./min and held at 60° C. for 5 minutes. The temperature was increased from 60° C. to 100° C. at 14° C./min, and held at 100° C. for 1 hour. The temperature was then increased from 100° C. to 120° C. at 7° C./min, and held at 120° C. for 1.5 hours. The temperature was then increased from 120° C. to 450° C. at 10° C./min and held at 450° C. for 3 hours. Following calcination, catalyst sample was allowed to cool down to room temperature and stored for testing.

Catalyst Testing:

The Pt/Ni/Al$_2$O$_3$ sample was tested as a catalyst for the conversion of glucose to ethylene glycol, propylene glycol and glycerol. 10 wt % glucose in water was used as feed with Hydrogen as co feed at 50 SCCM. The reaction was conducted in a fixed bed reactor, in trickle flow, top down approach. Prior to reactor entrance a preheating zone was included to heat feed to desired temperature. The catalyst was filled in the center of reactor with inert glass beads as filler materials on top and bottom of the reactor. A 5 micron metal frit was used at the bottom of reactor to secure catalyst in place. 5 grams of catalyst was loaded with a flow rate of liquid 10 wt % glucose in water varying from 2.5 to 10 ml/hr. The temperature was varied from 150 to 200 C and pressure from 450 to 750 PSIG.

Figure 7:
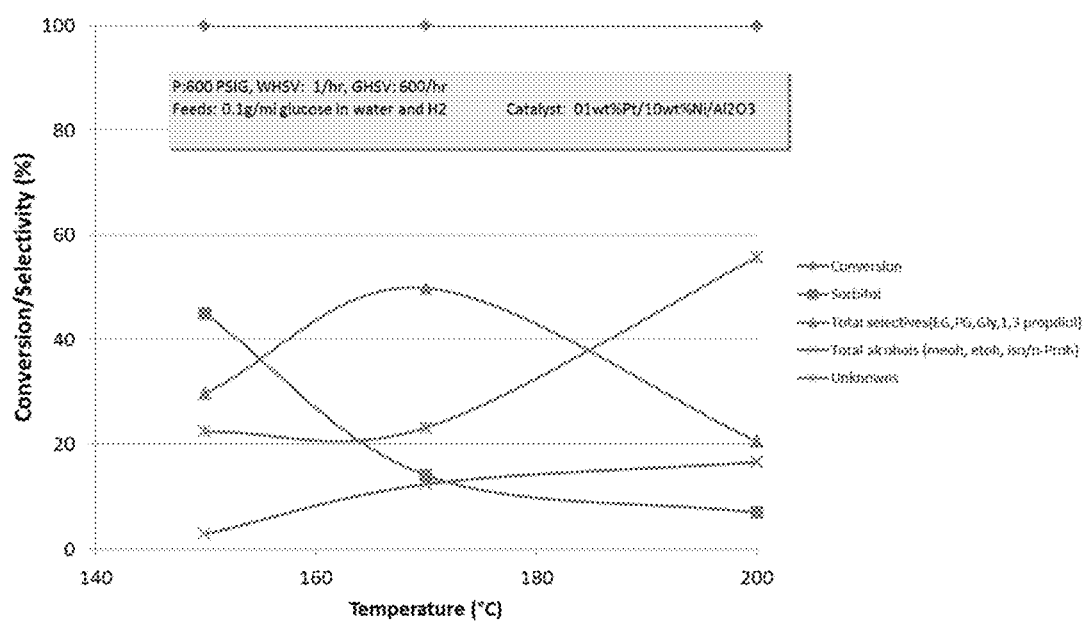
FIG. 7 shows the glucose conversion to glycols as a function of temperature for catalyst 1).

The results of the experiments described above are shown in FIGS. 7-9 are for catalyst 1) described above. FIG. 7 shows the glucose conversion to glycols as a function of temperature for catalyst 1). The data in FIG. 7 was produced using the following conditions: WHSV—1/hr, GHSV—600/hr, Pressure 600 PSIG, Feed of 10 wt % glucose and H$_2$. The selectivity for the production of ethylene glycol, propylene glycol, and glycerol was highest between 160° C. and 180° C.

Figure 8:
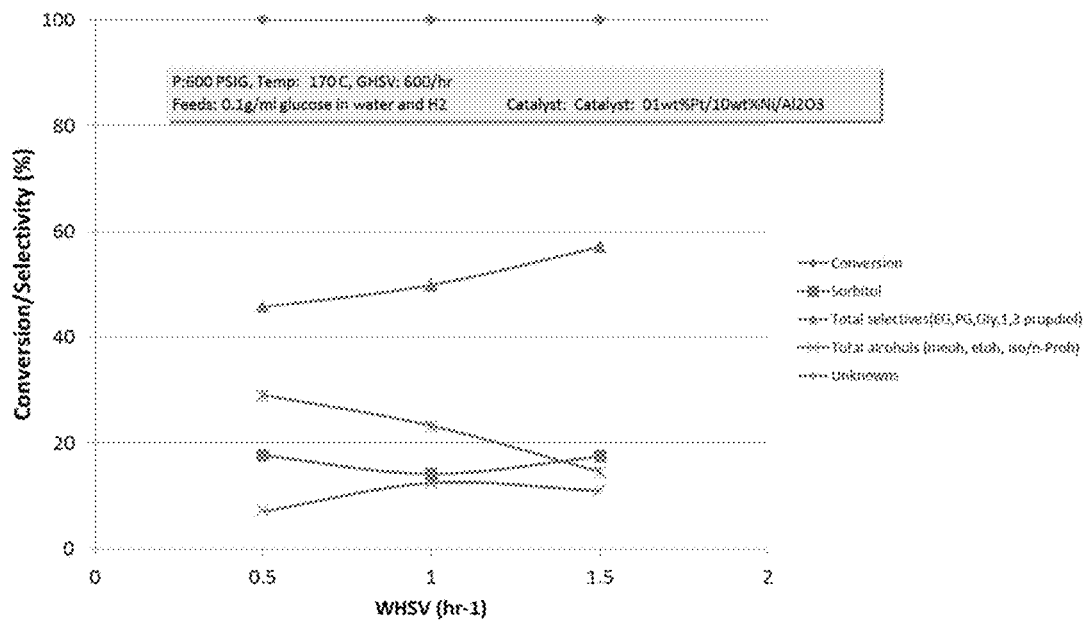
FIG. 8 shows the glucose conversion to glycols as a function of WHSV for catalyst 1).

FIG. 8 shows the glucose conversion to glycols as a function of WHSV for catalyst 1). The data in FIG. 8 was produced using the following conditions: GHSV—600/hr, Pressure 600 PSIG, Temperature 170° C. Feed of 10 wt % glucose and H$_2$. The selectivity for the production of ethylene glycol, propylene glycol, and glycerol was highest at a WHSV of 1.5/hr.

Figure 9:
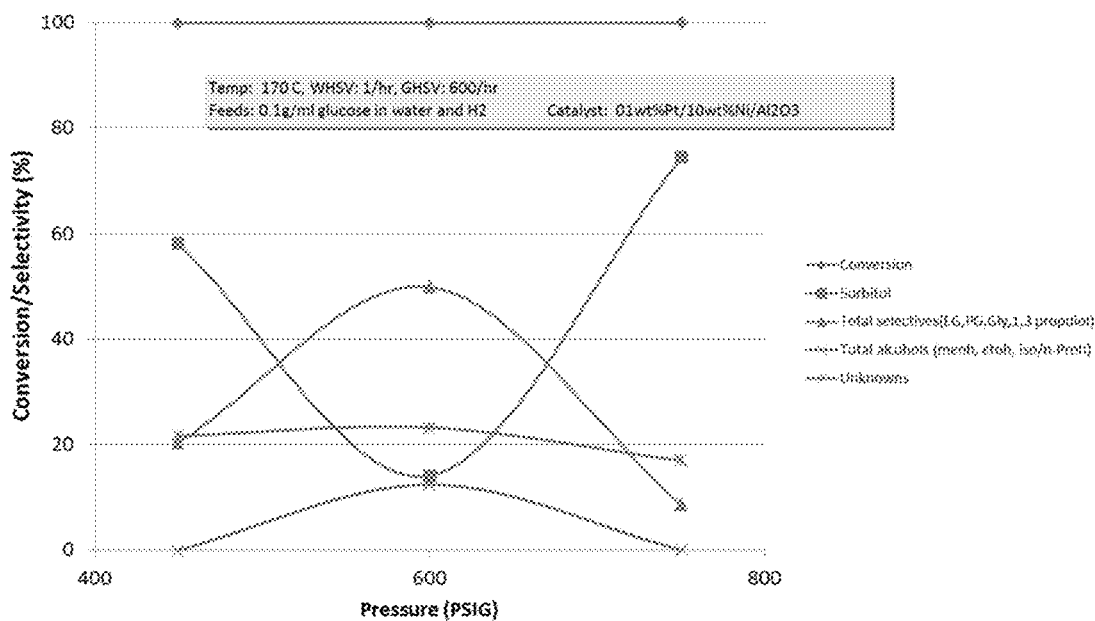
FIG. 9 shows the glucose conversion to glycols as a function of pressure for catalyst 1).

FIG. 9 shows the glucose conversion to glycols as a function of pressure for catalyst 1). The data in FIG. 9 was produced using the following conditions: WHSV—1/hr, GHSV—600/hr, Temperature 170° C. Feed of 10 wt % glucose and H$_2$. The selectivity for the production of ethylene glycol, propylene glycol, and glycerol was highest at a pressure between 550 and 650 psig.

FIG. 10 shows that Catalyst 3) was stable for more than 100 hours with a 100% conversion in a reaction under the following conditions: WHSV—1/hr (0 to about 50 hrs), 0.5 hr-1 (from about 50 hrs to about 115 hrs), 0.25 hr-1 (from about 115 hrs to about 120 hrs), GHSV—600/hr, Temperature 170° C. Feed of 10 wt % glucose in water and H$_2$. Pressure 600 psig. FIG. 10 also shows the selectivity for the production of ethylene glycol, propylene glycol, and glycerol over the course of the reaction.

FIG. 11 shows the selectivity of Catalyst 3) for the production of ethylene glycol, propylene glycol, and glycerol, as compared to the selectivity of sorbitol and unknowns over the course of the reaction as described for FIG. 10. The selectivity for ethylene glycol, propylene glycol, and glycerol, as compared to the selectivity of sorbitol and unknowns was stable over the course of the reaction.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:

1. A method comprising the step of:
    a) contacting a first product comprising ethylene glycol, propylene glycol, and glycerol with a catalyst composition, thereby producing a second product comprising acrolein and acetaldehyde, wherein the catalyst composition comprises a catalyst having the formula:

$M1M2_xM3_yO_z$ wherein M1 is a metal promoting dehydrogenation and C—O cleavage,
    wherein M2 is a metal with acid sites promoting dehydration,
    wherein M3 is an amphoteric catalyst support, with acid and base sites, promoting both dehydration and dehydrogenation in conjunction with M1,
    wherein x is a molar ratio from about 0.25 to about 4,
    wherein y is a molar ratio from about 0.25 to about 4,
    wherein z is the total amount of oxygen bound to M1, M2, and M3 and corresponds to the sum of the oxidation states of ML M2, and M3.

2. The method of claim 1, wherein the method further comprises the steps of:
    b) separating at least a portion of the acetaldehyde from the second product; and
    c) following step b) converting at least a portion of the acrolein in the second product to acrylonitrile.

3. The method of claim 1, wherein the first product is produced from C5 and/or C6 sugars in a single step using a multifunctional catalyst.

4. The method of claim 3, wherein the C5 and/or C6 sugars is C5 and/or C6 hemicellulose and cellulose derived sugars.

5. The method of claim 1, wherein from about 10 wt % to about 90 wt % of the propylene glycol and glycerol in the first product are converted to acrolein.

6. The method of claim 1, wherein the second product comprises from about 20 wt % to about 75 wt % of acrolein.

7. The method of claim 3, wherein the multifunctional catalyst comprises one or more metals selected from the group consisting of Cu, Zn, Sn, Ni, Pt, Pd, Ru, and Re, and a support.

8. The method of claim 7, wherein the support is selected from the group consisting of $Al_2O_3$, $SiO_2$, carbon, $TiO_2$, and MgO.

9. The method of claim 1, wherein step a) is performed at atmospheric pressure.

10. The method of claim 1, wherein M1 is selected from the group consisting of Cu, Zn, and Sn.

11. The method of claim 1, wherein M2 is selected from the group consisting of W and Fe.

12. The method of claim 1, wherein M3 is selected from the group consisting of Zr, Al, Si, Mg, Ti, La, and Ce.

13. The method of claim 1, wherein x is from about 0.8 to about 2.2.

14. The method of claim 1, wherein y is from about 0.8 to about 2.2.

15. The method of claim 1, wherein M1 is Cu.

16. The method of claim 1, wherein M2 is W.

17. The method of claim 1, wherein M3 is Zr.

18. The method of claim 1, wherein the catalyst has the formula $CuOWO_3ZrO_2$, or $CuOWO_3TiO_2$, or $CuOWO_3SiO_2$.

19. A method comprising the step of:
    a) contacting a first product comprising ethylene glycol, propylene glycol, and glycerol with a catalyst composition, thereby producing a second product comprising acrolein and acetaldehyde, wherein the catalyst composition comprises a catalyst having the formula:

$M1M2_xM3_yO_z$ wherein M1 is a metal promoting dehydrogenation and C—O cleavage,
    wherein M2 is a metal with acid sites promoting dehydration,
    wherein M3 is an amphoteric catalyst support, with acid and base sites, promoting both dehydration and dehydrogenation in conjunction with M1,
    wherein x is a molar ratio from about 0.25 to about 4,
    wherein y is a molar ratio is about 11,
    wherein z is the total amount of oxygen bound to M1, M2, and M3id corresponds to the sum of the oxidation states of M1, M2, and M3.

20. The method of claim 19, wherein the method further comprises the steps of:
    b) separating at least a portion of the acetaldehyde from the second product; and
    c) following step b) converting at least a portion of the acrolein in the second product to acrylonitrile.

* * * * *